(12) United States Patent
Liao et al.

(10) Patent No.: US 9,924,259 B2
(45) Date of Patent: Mar. 20, 2018

(54) EARPLUG-TYPE EARPHONE

(71) Applicant: Well Being Digital Limited, Hong Kong (HK)

(72) Inventors: Guoqiang Liao, Hong Kong (HK); Ming Yip Wong, Hong Kong (HK); Chor Tin Ma, Hong Kong (HK)

(73) Assignee: Well Being Digital Limited, Hong Kong (HK)

( * ) Notice: Subject to any disclaimer, the term of this patent is extended or adjusted under 35 U.S.C. 154(b) by 0 days.

(21) Appl. No.: 15/165,077

(22) Filed: May 26, 2016

(65) Prior Publication Data
US 2016/0269815 A1 Sep. 15, 2016

Related U.S. Application Data

(62) Division of application No. 13/319,441, filed as application No. PCT/CN2009/074953 on Nov. 16, 2009, now Pat. No. 9,392,351.

(30) Foreign Application Priority Data

May 18, 2009 (CN) ..................... 2009 2 0131840 U

(51) Int. Cl.
*A61B 5/1455* (2006.01)
*H04R 1/10* (2006.01)
*A61B 5/024* (2006.01)
*A61B 5/00* (2006.01)
*H04R 3/00* (2006.01)

(52) U.S. Cl.
CPC ......... *H04R 1/105* (2013.01); *A61B 5/02433* (2013.01); *A61B 5/02438* (2013.01); *A61B 5/14552* (2013.01); *A61B 5/6803* (2013.01); *A61B 5/7278* (2013.01); *A61B 5/742* (2013.01); *H04R 1/1016* (2013.01); *H04R 1/1033* (2013.01); *H04R 1/1058* (2013.01); *H04R 3/00* (2013.01); *A61B 5/1455* (2013.01); *H04R 1/1066* (2013.01)

(58) Field of Classification Search
None
See application file for complete search history.

(56) References Cited

U.S. PATENT DOCUMENTS 6,819,762 B2 11/2004 Jones
2010/0331631 A1 12/2010 MacLaughlin

FOREIGN PATENT DOCUMENTS

CN 200944657 9/2007

OTHER PUBLICATIONS

English Abstract of CN 200944657 (2 pages).

*Primary Examiner* — Eric Winakur
*Assistant Examiner* — Marjan Fardanesh
(74) *Attorney, Agent, or Firm* — Ware, Fressola, Maguire & Barber LLP

(57) ABSTRACT

An earplug-type earphone is disclosed including: an earplug (10) for producing sound and an elastic support (30). The earplug (10) includes a front housing (200) and a rear housing (500) connected in that order. The elastic support (30) is positioned on an outer side of the rear housing (500). When the earplug (10) is inserted in the external auditory canal, the elastic support (30) is pressed and deformed and then applies resilience to the helix, by which the earplug can be stably positioned in the external auditory canal.

5 Claims, 4 Drawing Sheets

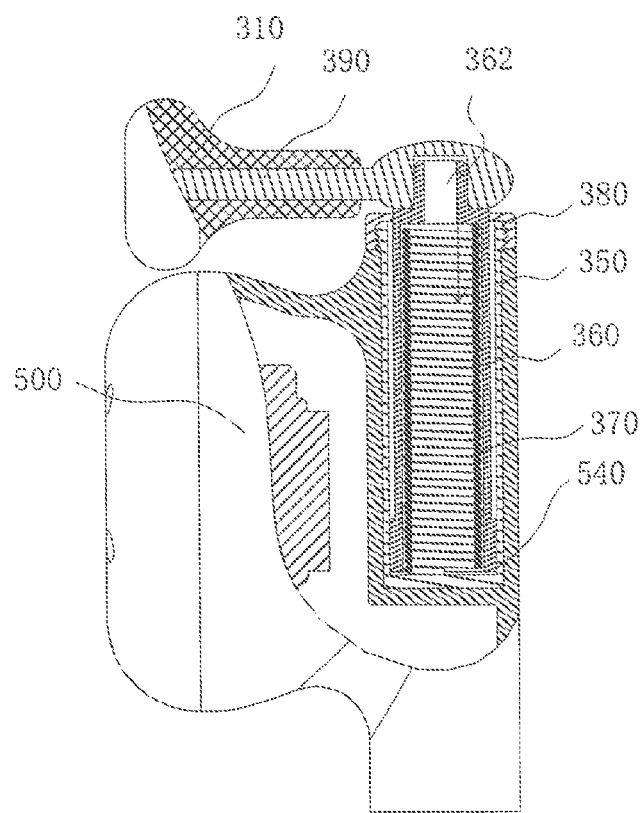
FIG. 4
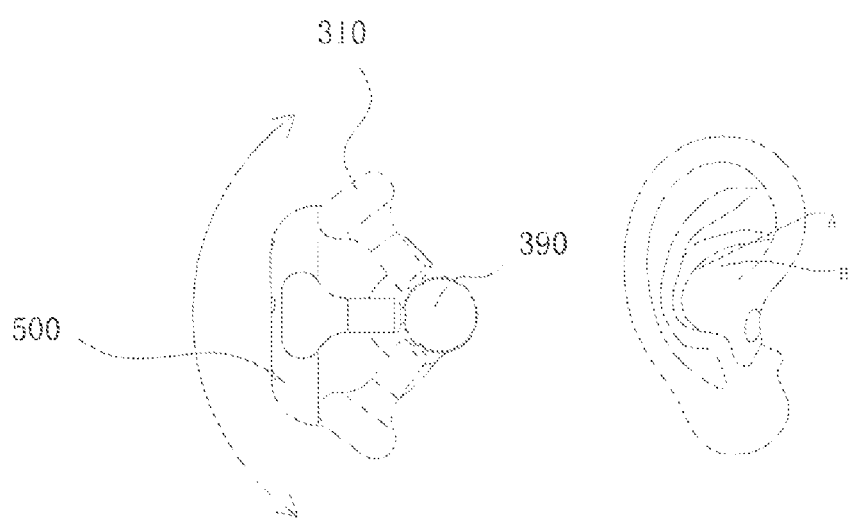
FIG. 5
FIG. 6

EARPLUG-TYPE EARPHONE

FIELD OF THE INVENTION

The present disclosure relates to earphones, and more particularly relates to an earplug-type earphone.

BACKGROUND OF THE INVENTION

Earplug-type earphone has become the most popular earphone in the industry due to its small size, convenience, and excellent performance. However, one major issue of the earplug type earphone is that the earplug of the earphone may become loose or displace from the ear canal when the connection wire is subject to small forces, such as gravity or touching, thus result in an insufficient volume and poor performance which needs readjustment. On the other hand, the earphone may also displace during the exercise of the wearer, such that the volume varies along with the rhythm. One way to overcome these issues is to use the headphone, which, however, is large, heavy and awkward to use. Another way is to add an ear hook to the earphone which fits around the top of the wearer's ear between the helix of the ear and the side of the wearer's head. While it corrects for the instability problem, the ear hook sacrifices convenience and comfort due to the friction between the hook and the helix of the ear.

Therefore, there is a need for improvement to overcome the issues above.

SUMMARY OF THE INVENTION

In one aspect of present disclosure, an earplug-type earphone is provided having a small size, good shock absorption, and an improved stability in use.

An earplug-type earphone includes: an earplug for producing sound; and an elastic support positioned on a sidewall of the carping.

In a preferred embodiment, the earplug includes a front housing and a rear housing connected in sequential order, the elastic support is positioned on an outer side of the rear housing.

In a preferred embodiment, the elastic support is attached to the earplug by an adhesive.

In a preferred embodiment, the earplug includes a protrusion to latch the elastic support.

In a preferred embodiment, the protrusion includes a top end away from the earplug having a greater size than that of a bottom end thereof close to the earplug, the protrusion further forms a stepped portion positioned between the top end and the bottom end; the elastic support defines a latching groove to match the protrusion.

In a preferred embodiment, the protrusion is columnar; the elastic support defines an inverted Y-shaped latching groove from the outside in to match the protrusion.

In a preferred embodiment, the rear housing defines a blind hole to receive an end of the elastic support.

In a preferred embodiment, the elastic support includes: an external sleeve positioned on the top of the blind hole; an internal sleeve positioned on the bottom of the external sleeve; an spring having two ends fixed to the external sleeve and the internal sleeve respectively; and a threaded flange to fix the external sleeve; wherein the internal sleeve extends through the threaded flange.

In a preferred embodiment, the elastic support further includes a rotation arm with one end thereof sleeved on the top of the internal sleeve and an elastic member positioned at the other end of the rotation arm.

In a preferred embodiment, the rotation arm forms an external thread, the elastic member defines a threaded hole to receive the rotation arm.

In a preferred embodiment, the earplug-type earphone further includes a vital signs measurement device positioned on the earplug.

In a preferred embodiment, the front housing of the earplug defines a groove, the vital signs measurement device comprises a light source and a light measuring device received in the groove, the vital signs measurement device further comprises a control device connected to the light source and a display device connected to the light measuring device.

When wearing the earplug-type earphone, the earplug can successfully enter the ear canal, because the elastic support positioned on a sidewall of the earplug can be deformed. When the earplug is in position, the elastic support releases the resilience and applies the force on the pinna, such that the earplug can be steadily held inside the ear canal and avoids sliding.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

FIG. 4 is a sectional view of one embodiment of the elastic support;

FIG. 5 shows the rotation of the rotation arm of the elastic support;

FIG. 6 shows a detailed anatomy of the outer ear;

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
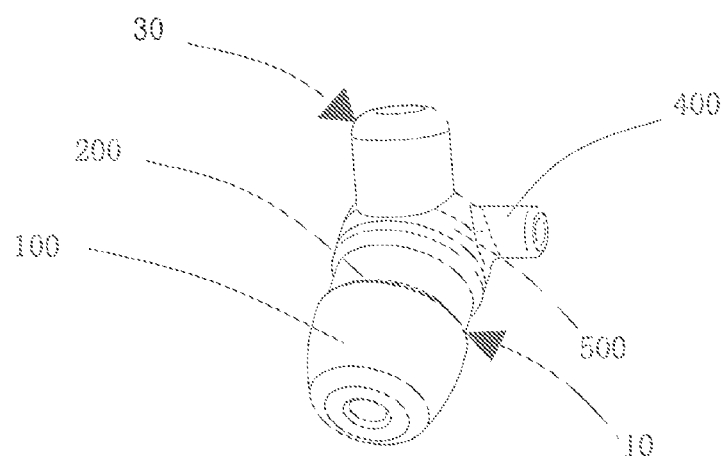
FIG. 1 is an isometric perspective view of an embodiment of an earplug-type earphone.

Referring to FIG. 1, an embodiment of the earplug-type earphone includes an earplug 10 for producing sound, an elastic support 30, a connection wire, and a plug (both not shown). The earplug 10 includes a front housing 200 and a rear housing 500 connected in sequential order. The front housing 200 is an audio housing. The front housing 200 and the rear housing 500 are usually made of rigid plastic.

The earplug-type earphone further includes a plug head 00 sleeved on the top of the front housing 200. The plug head 100 is usually made of soft materials such as silicone. When the earplug 10 is placed inside the ear canal, mainly the plug head 100 contacts an inner side of the ear canal, and the soft plug head 100 can increase ergonomic comfort.

The earplug-type earphone further includes a wire connection portion 400 positioned at the end of the rear housing 500 for interconnecting the connection wire and an internal circuit of the earplug 10. When the earplug 10 is placed inside the ear canal, the wire connection portion 400 will not contact the inner side of the ear canal due to the rear position of the rear housing 500.

The elastic support 30 is positioned on an outer side of the rear housing 500. In the illustrated embodiment, the elastic support 30 is cylindrical. In alternative embodiments, the elastic support 30 may be hemispherical, ellipsoid, or truncated cone-shaped. The elastic support 30 is attached to the outer side of the rear housing 500 by an adhesive, or it may be latched to the earplug 10.

Figure 2:
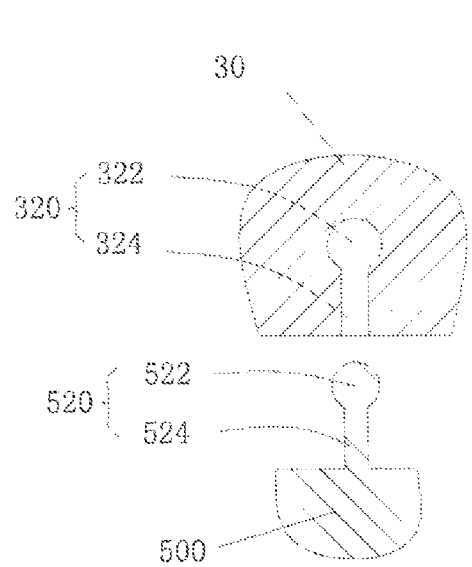
FIG. 2 shows a latch structure of one embodiment of the elastic support.

Referring to FIG. 2, the earplug 10 further includes a protrusion 520 positioned on the outer side of the rear housing 500. The protrusion 520 may be integrally formed with the rear housing 500, and it may be made of material more rigid than that of the elastic support 30. The protrusion 520 includes a top end 522 away from the rear housing 500 and a bottom end 524 close to the rear housing 500. The top end 522 has a greater size than that of the bottom end 524. The protrusion 520 further forms a stepped portion positioned between the top end 522 and the bottom end 524. The elastic support 30 defines a latching groove 320 to latch the protrusion 520. The latching groove 320 includes a head portion 322 close to the inside of the latching groove 320 and a tail portion 324 close to the outer side of the elastic support 30. The head portion 322 has a shape matching the top end 522 of the protrusion 520, and the tail portion 324 has a shape matching the bottom end 524 of the protrusion 520. Since the elastic support 30 is flexible, the top end 522 of the protrusion 520 can easily extend through the tail portion 324 of the latching groove 320 and reach the head portion 322. After the top end 522 reaching the head portion 322, the step portion between the top end 522 and the bottom end 524 ensure that the top end 522 is firmly received in the head portion 322, such that the elastic support 30 is fixed to the outer side of the rear housing 500. In order to achieve a better latching performance, the tail portion 324 of the latching groove 320 is preferred interference fit with the bottom end 524 of the protrusion 520, i.e. the protrusion 520 has a greater size than that of the latching groove 320.

Figure 3:
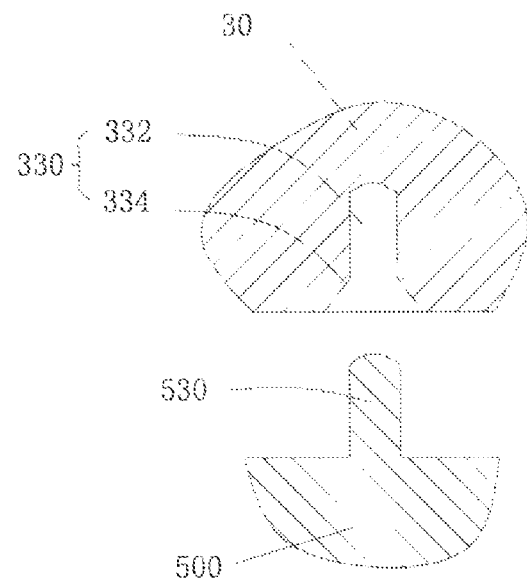
FIG. 3 shows a latch structure of another embodiment of the elastic support.

In alternative embodiments, the protrusion 520 and the latching groove 320 may be threaded connected or in a way shown in FIG. 3. In FIG. 3, the protrusion 530 is columnar, and the latching groove 330 is inverted Y-shaped from the outside in. In other words, the head portion 332 of the latching groove 330 is columnar and is interference fit with the protrusion 530, and the tail portion 334 has a gradually enlarged opening to help entering of the protrusion 530. After the protrusion 530 reaches the head portion 332 of the columnar latching groove 330, the interference fit between them ensure that the protrusion 530 is firmly received in the latching groove 330, such that the elastic support 30 is fixed to the outer side of the rear housing 500.

In alternative embodiments, the positions of the protrusion 520 and the latching groove 320 may be exchanged with each other, i.e. the protrusion 520 may positioned on the elastic support 30, while the latching groove 320 may defined on the rear housing 500. The elastic support 30 may be connected to the rear housing 500 via unlimited ways, as long as the elastic support 30 can be firmly attached to the rear housing 500.

The number of the elastic support 30 may be more than one, such as two, to make sure the earplug is aligned with the ear canal. The elastic support 30 is preferred made of soft materials which tend to be elastic deformation but not plastic deformation, such as memory foam. The soft memory foam can be elastically deformed to increase the comfort, and it can increase the durability for no plastic deformation.

When the earplug 10 enters the ear canal, the pinna may resist the elastic support 30. However, the earplug 10 will successfully enter the ear canal because the elastic support 30 can be deformed. When the earplug 10 is in position, the elastic support 30 releases the resilience and applies the force on the pinna, such that the earplug 10 can he steadily held inside the ear canal and avoids sliding out of the ear canal. The height of the elastic support 30 should be carefully and properly chosen to ensure there is an interference fit between the elastic support 30 and the pinna. Excess height of the elastic support 30 will result in that the elastic support 30 may not be able to fit in the pinna due to the limited deformation, and insufficient height of the elastic support 30 will lead to the failure of immobilization of the earplug 10 in the ear canal due to the insufficient resilience of the earplug 10.

In the previously description, in use, the elastic support 30 resists only one place in the external helix directly. In order to increase the number of supporting points, in alternative embodiments, the elastic support 30 may have different structures.

Figure 8:
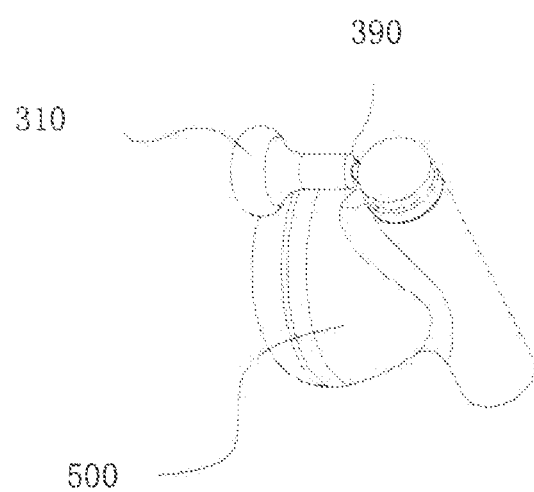
FIG. 8 is an isometric perspective view of the elastic support of FIG. 4.

Referring to FIG. 4 and FIG. 8, the rear housing 500 defines a blind hole 540 on the top end. The elastic support 30 includes an external sleeve 350 with an upper opening, an internal sleeve 360 with a bottom opening, a spring 370, and a threaded flange 380. The external sleeve 350 has an external thread on the top, and the external sleeve 350 is fixed inside the blind hole 540 via the threaded flange 380. The internal sleeve 360 extends through the threaded flange 380 and is received in the external sleeve 350. One end of the spring 370 is fixed to the bottom of the external sleeve 350, the other end is fixed to the top of the internal sleeve 360, such that the internal sleeve 360 is capable of sliding inside the external sleeve 350 in the range of the resilience of the spring 370.

The elastic support 30 further includes an elastic member 310 positioned on top of the internal sleeve 360. When wearing the earplug 10, the internal sleeve 360 is firstly pressed, after the earplug 10 is in position, the internal sleeve 360 is released and resists the helix by the resilience of the elastic member 310, thus fixing the earplug 10.

In order to position the elastic member 310, a protruding post 362 is provided on top of the internal sleeve 360. The elastic support 30 further includes a rotation arm 390 having one end sleeved on the protruding post 362, such that the rotation arm 390 is capable of rotating for 360 degrees along a radial plane of the protruding post 362, as shown in FIG. 5.

The elastic member 310 is positioned at the other end of the rotation arm 390. Referring to FIG. 4, the rotation arm 390 forms an external thread on its surface, the elastic member 310 defines a threaded hole to receive the rotation arm 390, such that the position of the rotation arm 390 relative to the elastic member 310 is adjustable.

Referring to FIG. 6, when in use, the rotation arm 390 is firstly pressed and drives the internal sleeve 360 to compress the spring 370. When the earplug 10 enters the ear canal, the rotation arm 390 is released and rises along with the internal sleeve 360 by the resilience of the spring 370, then the rotation arm 390 resists an A position (anti-helix) of the outer ear, and the elastic member 310 is latched at a B position of the outer ear. Since the earplug 10 is provided with two supports from two orthogonal directions, it is firmly positioned in the ear. The wearer can also adjust the rotation angle of the rotation arm 390 and the position of the rotation arm 390 relative to the elastic member 310 to get a more comfortable state.

The earplug-type earphone described above has a simple structure and a relatively small size, and it can avoid sliding or falling off the ear. In addition, the elastic support can absorb shock to the earplug during the excises or movements.

Figure 7:
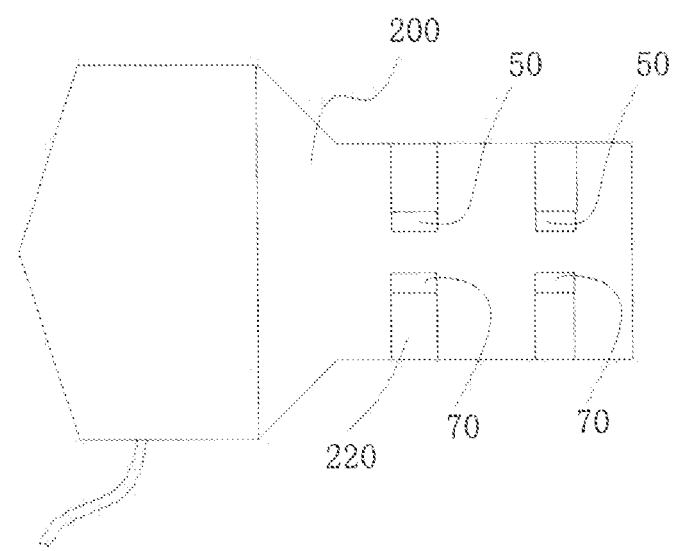
FIG. 7 shows a earplug with a vital signs measurement device.
Figure 9:
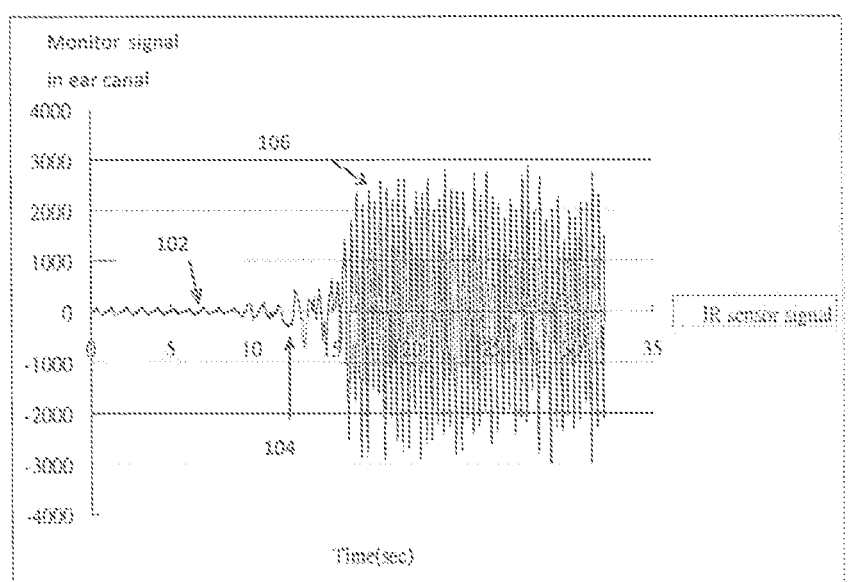
FIG. 9 is a heartbeat signal diagram generated by the earplug-type earphone.

The present disclosure further discloses an earphone having vital signs measurement device which can monitor the vital signs during the excises. Referring to FIG. 7, the front housing 200 of the earplug 10 defines at least one groove 220, and the plug head 100 defines an opening corresponding to the groove 220. The vital signs measurement device includes a light source 50 and a light measuring device 70 received in the groove 220. The vital signs measurement device further includes a control device connected to the light source 50 and a display device (such as screen of MP3) connected to the light measuring device 70 via a signal wire. The light source 50 is controlled by the control device to emit light signals, e.g., red light and infrared, to the skin of the ear canal. Since the microvascular of the skin expands and contracts along with the heart beat and the skin of the ear canal is very thin, the light signals will be modulated by the heart beat signals and will be reflected. The light measuring device 70 receives and analyses the reflected light signals to extract the heart beat information, which will then be displayed on the display device. This earphone is preferred be provided with a shock absorption mechanism, because the variation of the reflect light is tiny, for the expansion and contract of the microvascular of the skin are tiny. Vigorous physical activities, such as running, will cause a great fluctuation of the angle and the intensity of the reflected light, thus the result obtained by the light measuring device 70 based on the electrical signal may be not correct. FIG. 9 shows an IR LED raw signal diagram of a test generated by the earplug-type earphone. During the test, the state of the wearer changes from static to motion. According to FIG. 9, when the wearer is under a static state (in section 102), the raw signal precisely corresponds to the heartbeat signals. However, when the wear starts to run (in section 104), the heartbeat signals are covered by noises produced by motion, which has an amplitude much larger than that of the heartbeat signals (in section 106). Accordingly, as for the earphone with vital signs measurement device, it is necessary to introduce the shock absorption mechanism to reduce the vibration of the earplug in the ear canal, so as to greater suppress the noise of the heartbeat signals caused by the motion.

This type of the earphone with the vital signs measurement device includes the elastic support as previously described, such that the motion and the shock of the earplug in the ear canal can be reduced, and an accuracy of the measurement device is increased.

Although the invention has been described in language specific to structural features and/or methodological acts, it is to be understood that the invention defined in the appended claims is not necessarily limited to the specific features or acts described. Rather, the specific features and acts are disclosed as sample forms of implementing the claimed invention.

The invention claimed is:

1. An earplug-type earphone, comprising:
    an earplug adapted for insertion into a canal of an ear of a user; and
    a flexible elongate arm member located on the earplug and having a distal end biased to press in a direction against an anti-helix part of the ear when the earplug is inserted into the ear canal of the user;
    wherein the distal end of the flexible elongate arm member is rotatable within a plane generally orthogonal to the direction of the bias.

2. An earplug type earphone as claimed in claim 1, wherein the arm member is moveable relative to the earplug in the direction against the anti-helix part of the ear.

3. An earplug-type heart rate monitor, comprising:
    an earplug adapted for insertion into the canal of an ear of a user;
    a light source and a light measuring device being incorporated in the earplug;
    the light source adapted for sending light signals into a surface of the ear canal, the light signals being detected by the light measuring device; and
    an arm member on the earplug, the arm member having a distal end biased for pressing against an anti-helix part of the ear when the earplug is inserted into the ear canal of the user, wherein the distal end of the arm member is rotatable in a plane generally orthogonal to the to a direction of the bias.

4. An earplug-type heart rate monitor as claimed in claim 3, wherein the light source includes an infrared light source, a red light source, or both.

5. An earplug-type heart rate monitor as claimed in 3, wherein the is moveable arm member relative to the earplug in the direction against the anti-helix part of the ear.

* * * * *